US006956196B2

(12) United States Patent
Duhon (10) Patent No.: US 6,956,196 B2
(45) Date of Patent: Oct. 18, 2005

(54) SYSTEMS FOR MAINTAINING THE SPATIAL POSITION OF AN OBJECT AND RELATED METHODS

(75) Inventor: John G. Duhon, Lafayette, LA (US)

(73) Assignee: Oncology Automation, Inc., Lafayette, LA (US)

( * ) Notice: Subject to any disclaimer, the term of this patent is extended or adjusted under 35 U.S.C. 154(b) by 197 days.

(21) Appl. No.: 10/257,520

(22) PCT Filed: Apr. 10, 2001

(86) PCT No.: PCT/US01/11615

§ 371 (c)(1),
(2), (4) Date: Oct. 11, 2002

(87) PCT Pub. No.: WO01/76692

PCT Pub. Date: Oct. 18, 2001

(65) Prior Publication Data

US 2003/0053075 A1 Mar. 20, 2003

Related U.S. Application Data

(60) Provisional application No. 60/195,823, filed on Apr. 11, 2000.

(51) Int. Cl.$^7$ ................................................. H01J 40/14
(52) U.S. Cl. .................................... 250/221; 250/559.3
(58) Field of Search .............................. 250/221, 223 R, 250/559.4, 559.29, 559.3, 370.09, 370.08, 370.1; 128/653.2; 378/4, 20

(56) References Cited

U.S. PATENT DOCUMENTS

| | | | |
|---|---|---|---|
| 3,733,129 A | 5/1973 | Bridges | |
| 3,740,141 A | 6/1973 | DeWitt, Jr. | |
| 4,647,206 A | 3/1987 | Kunzmann et al. | |

(Continued)

FOREIGN PATENT DOCUMENTS

| | | |
|---|---|---|
| DE | 3926549 C1 | 2/1991 |
| DE | 4303804 A1 | 8/1994 |
| DE | 4418216 A1 | 11/1995 |

(Continued)

OTHER PUBLICATIONS

Bien; F. et al.; "Absolute Distance Measurements By Variable Wavelength Interferometry" Applied Optics; Feb. 1, 1981; vol. 20; No. 3; pp. 400–403.

Cheng, Yeou–Yen et al.; "Multiple–Wavelength Phase–shifting Interferometry"; Applied Optics; Mar. 15, 1985; vol. 24; No. 6; pp. 804–807.

(Continued)

Primary Examiner—Que T. Le
(74) Attorney, Agent, or Firm—Siebert & Patty, L.L.C.

(57) ABSTRACT

Apparatus for correcting positional deviations of at least one area of a subject along one or more subject position axes. The apparatus comprises: (a) a distance-measuring component which employs a phase difference between two oscillatory signals to measure and monitor changes in the position of a subject area; (b) storage means for storing information corresponding to the prior and later spatial positions of the area; (c) a support upon which the subject may lie; (d) calculating means for determining, from the stored information, a deviation in spatial position of the area from its prior spatial position along the first subject position axis and translatory motion of the area which will restore the area to its prior spatial position along the first subject position axis, and generating at least one repositioning signal which transmits information corresponding to the translatory motion of either the support or the area necessary to restore the area to its prior spatial position along the first subject position axis; and (e) a position controller which can at least reposition the support in response to the repositioning signal.

39 Claims, 3 Drawing Sheets

U.S. PATENT DOCUMENTS

| | | |
|---|---|---|
| 5,054,912 A | 10/1991 | Kuchel |
| 5,130,523 A | 7/1992 | Raleigh et al. |
| 5,164,602 A | 11/1992 | Lettang |
| 5,446,548 A | 8/1995 | Gerig et al. |
| 5,553,112 A | 9/1996 | Hardy et al. |
| 5,589,928 A | 12/1996 | Babbitt et al. |
| 5,727,042 A | 3/1998 | Brenneisen |
| 5,970,113 A * | 10/1999 | Crawford et al. ............ 378/19 |

FOREIGN PATENT DOCUMENTS

| | | |
|---|---|---|
| DE | 19614643 A1 | 10/1997 |
| DE | 19728788 A1 | 1/1999 |
| EP | 0529311 A1 | 3/1993 |

OTHER PUBLICATIONS

Geimini, E. et al.; "Tunable, Double–wavelength Heterodyne Detection Interferometer for Absolute–distance Measurements"; Optics Letters; Feb. 1, 1994; vol. 19; No. 3; pp. 213–215.

Polhemus, C.; "Two–wavelength Interferometry"; Applied Optics; Sep. 1973; vol. 12; No. 9; pp. 2071–2074.

Rogus, Ronald D. et al.; "Accuracy of a Photogrammetry-based Patient and Monitoring System for Radiation Therapy"; Medical Physics; May 1999; vol. 26; No. 5; pp. 721–728.

Woodbury, Neal et al.; "Frequency–Modulated Laser Ranging"; Website (visited Oct. 10, 2002) <http://www.phaselaser.com/sensor93.htm>; Publication date Sep. 1993, Sensors magazine; 4 pages.

* cited by examiner

SYSTEMS FOR MAINTAINING THE SPATIAL POSITION OF AN OBJECT AND RELATED METHODS

REFERENCE TO RELATED APPLICATIONS

This application is the National Stage of International Patent Appl. No. PCT/US01/11615 filed on Apr. 10, 2001, which in turn claims the benefit of U.S. Provisional Patent Appl. No. 60/195,823, filed on Apr. 11, 2000.

TECHNICAL FIELD

This invention relates to apparatus and methods for adjusting the spatial position of a subject supported by a position-adjustable support during radiation treatment or the performance of other acts upon the subject.

BACKGROUND

Maintaining the position of a subject while performing acts upon the subject can be of critical importance in certain circumstances. In the medical field, for example, during certain treatment procedures (e.g., radiation therapy procedures) it can be critical to effective treatment and safety that the area designated for treatment be positioned correctly and remain in place during the procedure. Incorrect initial positioning as well as excessive movement of the patient subject and associated target area designated for treatment without adjustment may result in the application of radiation to areas beyond the designated target area, in turn resulting in potentially ineffective, even harmful, treatment of the patient subject. Other medical treatment regimes and procedures, e.g., radiation therapy simulations and stereo tactic radio surgery, similarly call for the accurate targeting of areas upon the subject to insure accuracy, safety and effectiveness. Some methods which attempt to address these concerns are dependent upon mechanical measurement devices or retro reflective objects and surfaces to improve reflected signal strength to the signal receiver, while others which employ optical or sonic time-of-flight measurement techniques may not achieve the desired accuracy (e.g., margins of error of less than 1 mm at distances up to 5–7 meters).

A need thus exists for relatively simple yet effective and accurate apparatus and methods for maintaining the spatial position of a target area during application of medical treatment or during the performance of other acts upon a subject.

DEFINITIONS AND SUMMARY OF THE INVENTION

As used in this description and the appended claims, the following definitions apply:

"Subject" means any animate or inanimate object, with a medical patient being only one example of an animate object.

"Support" means a table, bed, cradle, platform or any other object which may be used to suspend at least a portion of a subject off of the ground.

Other terms which may call for further definition are set forth below when introduced.

The present invention is deemed to meet the above-described and other needs in a novel and highly effective way by providing, among other things, apparatus for detecting, measuring and correcting positional deviations of at least one area of a subject (an area being equal to one or more points of matter) along one or more subject position axes, from a prior spatial position at a prior time to a later spatial position at a later time. In one embodiment of this invention, the apparatus comprises:

(a) a distance-measuring component which at least
  1) continuously or intermittently gathers information corresponding to the spatial position of the area along a first subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area, and
  2) derives the later spatial positions, and optionally the prior spatial positions, of the area along the first subject position axis from the information gathered in 1);
(b) storage means for storing information corresponding to the prior and later spatial positions of the area;
(c) a support upon which the subject may lie;
(d) calculating means for determining from the stored information a deviation in spatial position of the area from its prior spatial position and translatory motion of the area which will restore the area to its prior spatial position, and generating at least one repositioning signal which transmits information corresponding to the translatory motion of either the support or the area necessary to restore the area to its prior spatial position; and
(e) a position controller which can at least reposition the support in response to the repositioning signal. In a preferred embodiment, the distance-measuring component only derives the later spatial positions of the area along the first subject position axis from the information gathered in 1), since the prior spatial position will be a predetermined set of distances entered into the storage means by the user to provide a target distance against which all future measurements are compared.

Through the use of determined phase differential between the first radiation beam before reflection by the target area and after reflection by the target area, the apparatus enables very accurate (preferably no more than 0.5 mm resolution, most preferably no more than 0.25 mm resolution, over target to sensor distances of up to 5 meters) measurement of deviations in spatial position of the target area without the use of adhesive reflection targets or other items placed upon the target area, and without the use of cameras, stereo tactic reference structures, or other devices.

In another embodiment, this invention provides apparatus for detecting, measuring and correcting positional deviations of at least three (and more preferably at least four) areas on a subject along at least three corresponding subject position axes, from prior spatial positions at a prior time to later spatial positions at a later time, respectively. The apparatus comprises storage means, a support, calculating means, and a controller as described herein, and further comprises a distance-measuring component which at least 1) continuously or intermittently gathers information corresponding to the spatial positions of the areas along their respective first, second and third subject position axes, the information for each area being comprised of a phase difference between two oscillatory signals, the first of the signals A) corresponding to the intensity modulation of, or B) bearing a phase relationship to, a first amplitude modulated beam of radiation before the first beam of radiation is incident upon the respective area, and the second of the signals A) corresponding to the intensity modulation of, or B) bearing a phase relationship to, the first beam of radiation after the first beam of radiation has been reflected by the respective area, and 2) derives later spatial positions, and optionally the later spatial positions, of the areas along the respective subject position axes from the information gathered in 1).

Yet another embodiment of this invention provides apparatus for enhancing a position-adjustable subject support which includes a position controller. The apparatus comprises (a) a distance-measuring component of this invention as described herein, (b) storage means of this invention as described herein; and (c) calculating means of this invention as described herein, all operating on a continuous or intermittent basis to provide rapid position deviation detection and position adjustment capabilities over a span of time. The embodiments of the invention referred to in this and in the immediately preceding paragraph enable real-time three-dimensional correction of subject movement to insure stable subject positioning during treatment.

This invention also provides in another embodiment a method of applying therapeutic radiation to a subject, the method comprising (a) providing a support upon which the subject may lie; (b) while the subject is on the support and receiving therapeutic radiation, continuously or intermittently gathering information corresponding to the spatial position of at least one area along at least one subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area; (c) deriving later spatial positions, and optionally the prior spatial positions, of the area along the subject position axis from the information gathered in (b); (d) storing information corresponding to the prior and later spatial positions derived in (c); (e) calculating from the stored information a deviation in spatial position of the area from its prior spatial position; (f) determining, from the stored information and/or the deviation calculated in (e), translatory motion of the area which will restore the area to the prior spatial position; (g) generating at least one repositioning signal which transmits information corresponding to the translatory motion of either the support or the area which is necessary to restore the area to the prior spatial position; and (h) repositioning the support in response to the repositioning signal.

Another embodiment of this invention is an apparatus for detecting, measuring and correcting positional deviations of at least one area of a subject along one or more subject position axes, from a prior spatial position at a prior time to a later spatial position at a later time, which includes a) a distance-measuring component which at least 1) continuously or intermittently gathers information corresponding to the spatial position of the area along a first subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area, and 2) derives the later spatial position, and optionally the prior spatial position, of the area along the first subject position axis from the information gathered in 1), b) a storage component for storing information corresponding to the prior and later spatial positions of the area, c) a support upon which the subject may lie, d) a calculating component for determining, from the stored information, a deviation in spatial position of the area from its prior spatial position along the first subject position axis and translatory motion of the area which will restore the area to its prior spatial position along the first subject position axis, and generating at least one repositioning signal which transmits information corresponding to the translatory motion of either the support or the area necessary to restore the area to its prior spatial position along the first subject position axis, and e) a position controller which can at least reposition the support in response to the repositioning signal.

These and other embodiments and features of the invention will become still further apparent from the ensuing description, appended claims and accompanying drawings.

BRIEF DESCRIPTION OF THE DRAWINGS

In each of the above figures, like numerals are used to refer to like or functionally like parts among the several figures.

DETAILED DESCRIPTION OF THE INVENTION

As will now be appreciated, apparatus and methods of this invention enable the detection of the direction and magnitude of movement in at least one area of a subject, the measurement of the magnitude of such movement, and automated adjustment of the position of the area to return the area to the desired spatial location. In this way, medical treatment or other acts maybe performed on an accurately positioned subject while minimizing the effects of detected subject movement. In addition, apparatus of this invention may be connected to control systems which perform the desired acts upon the subject (e.g., a control system for a linear accelerator applying radiation to the subject) to only allow delivery or application of treatment when the subject target area is within selected position tolerances.

It will be appreciated that the calculating means of this invention is preferably any device, apparatus, system or combination thereof capable of determining from the stored information a deviation in spatial position of the areas from their prior spatial positions and translatory motion of the areas which will restore the areas to their prior spatial positions, and generating at least one repositioning signal which transmits information corresponding to the translatory motion(s) of either the support or the areas which is (are) necessary to restore the areas to their prior spatial positions. The calculating means may be a single device which both determines the deviation in spatial position and the restorative translatory motion required, and generates the aforesaid repositioning signal, or it may be a combination of devices which each perform one or more of these tasks. Suitable non-limiting examples of calculating means include computers, electronic circuits, microprocessors, signaling devices or a combination thereof, with at least one suitably programmed computer being particularly preferred.

The calculating component of an embodiment of this invention is any device, apparatus, system or combination thereof capable of performing the functions required.

It will be appreciated that the storage means of this invention is preferably any device, apparatus, system or combination thereof capable of receiving and storing information for later retrieval. Suitable non-limiting examples of storage means include computer random access memory, magnetic media accessible by computer or computer network, and the like, including combinations thereof.

The storage component is any device, apparatus, system or combination thereof capable of receiving and storing information for later retrieval as required by an embodiment of this invention.

The distance-measuring component in embodiments of this invention may comprise any object, system, apparatus, device or combination thereof which is capable of at least continuously or intermittently gathering information in accordance with this invention and deriving the later spatial positions, and optionally the prior spatial positions, of a target area along a subject position axis from the information previously gathered. In preferred embodiments, the distance-measuring component only derives the later spatial positions, because the prior spatial position of the target area is predetermined, e.g., through use of a simulator, and entered into the storage means in advance of use of the distance-measuring component. In addition, the distance-measuring component preferably further at least simultaneously or sequentially repeats the gathering of information and derivation of spatial positions, using a second amplitude modulated beam of radiation reflected by at least one area which is either the same as or different from the previous area, the second amplitude modulated beam of radiation having a modulation frequency which is not a harmonic of the first beam of radiation. It is also preferred that the source of radiation beams in the distance-measuring component be comprised of one or more coherent light sources for generating the amplitude modulated beams of radiation, and more preferably is comprised of one or more lasers. Most preferably, the distance measuring component is comprised of the combination of one or more laser/sensor heads in communication with a computer component, both further described hereinafter.

The computer component of the preferred distance-measuring component of this invention is programmed and equipped to at least measure the phases of the two oscillatory signals, determine the difference between those phases, and, from this determined phase difference, calculate the prior and later spatial positions of the target area along a given subject position axis. The spatial positions of the target area along a given subject position axis are determined by measuring the distance from the laser to the target area at different moments in time. From a measured phase difference at a given moment in time, the distance from laser to target area at that moment in time may be calculated by a program residing, for example, in the sensor microprocessor, using the following relationship:

$$\Delta\phi = \frac{4\pi d}{\lambda} \quad (1)$$

where $\Delta\phi$=relative phase, d=distance, and $\lambda$=wavelength of the modulation. The phase difference between two modulated signals of the same frequency is time independent. One can therefore measure the phase difference over a time period much longer than the desired time resolution of, e.g., 10 picoseconds. In principle, the more cycles of the modulation over which the measurement is taken, the more accurate the result. This suggests that the two simple ways to increase the accuracy of the relative phase determination are to increase the time of the measurement, and/or decrease the wavelength (i.e., increase the frequency) of the modulation. When decreasing the wavelength, however, it will be noted that the relative phase of two sine waves is typically measured by multiplying the two signals together in an electronic mixer and then averaging the result of this multiplication over many modulation cycles.

Stated mathematically, this becomes:

$$\lim_{T\to\infty} \frac{1}{T} \int_0^T \sin\left(\frac{2\pi c}{\lambda}t + \frac{4\pi d}{\lambda}\right) \sin\left(\frac{2\pi c}{\lambda}t\right) dt \quad (2)$$

where d=distance to target, $\lambda$=wavelength, c=speed of light, t=time and T=averaging interval. Evaluating expression (2) including the gain of an integrated amplifier gives (3).

$$A\cos\left(\frac{4\pi d}{\lambda}\right) \quad (3)$$

where A=amplitude factor that depends upon the gain of the integrating amplifier. From the foregoing it is evident that it may be more precise to say that is not the phase itself that is actually measured, but rather the cosine of the phase. If the round-trip distance to be measured is larger than the modulation wavelength, then the cosine of the phase is no longer single valued. In other words, there will be more than one distance that corresponds to a given phase measurement:

$$\cos\phi = \cos\left(\frac{4\pi d}{\lambda}\right) = \cos\left[\frac{2\pi(x+n\lambda)}{\lambda}\right] \quad (4)$$

As shown in the above equation (4), $x+n\lambda$ is the true distance, but a single measurement of $\Delta\phi$ at $1\Delta$ does not uniquely determine both x and n. In order to remove this degeneracy when the round-trip distance to be measured is larger than the modulation wavelength, it is necessary to measure the relative phase for at least two different modulation frequencies, using the following expressions:

$$\cos\phi_1 = \cos\left[\frac{2\pi(x+n\lambda_1)}{\lambda_1}\right] \quad (5)$$

$$\cos\phi_2 = \cos\left[\frac{2\pi(x+n\lambda_2)}{\lambda_2}\right]$$

from which both x and n are uniquely determined, thus allowing the measurement of the true distance. However, there are regions of the cosine function given in Equation 4 that are much more sensitive than others to small changes in the distance. Mathematically speaking, the derivative of the measured value with respect to distance is dependent on distance, expressed as follows:

$$\frac{d(\cos\phi)}{dx} = -\frac{2\pi}{\lambda}\sin\left[\frac{2\pi(x+n\lambda)}{\lambda}\right] \quad (6)$$

From the above it can be seen that there will be certain values of the total distance (x+nλ) where the change of the measured value with respect to the distance is zero. In this region of the curve, the accuracy of the measurement will be very poor. To address this concern, additional information is acquired on each measurement by repeating the measurements at each modulation frequency with two different reference phases, separated by π/2. This way, for each measurement preformed in an insensitive region of the curve, a corresponding measurement will be performed in the sensitive region. The basic effect is to measure both the cosine and the sine of the phase. Between those two measurements, all of the information theoretically available at a particular modulation frequency is obtained.

In selecting a modulation frequency, factors include the distance to be measured and the accuracy desired. The higher the modulation frequency, the greater the accuracy. Beyond a point, however, higher modulation frequencies also imply more costly electronics components and more technical problems with shielding and stray capacitance in the circuit. Normally, the relevant constraint is the ability to measure distances of several tens of meters with accuracies of 1 mm or less resolution, preferably 0.5 mm or less resolution, and most preferably 0.25 mm or less resolution. Accuracies considered in this specification are based on 200–300 millisecond averaging times. Using a frequency in the range of 90 to 100 MHz is preferred for distances of 5–7 meters, and has the added advantage that the circuit can incorporate a transmitter and a receiver very similar in design to those used in radio wave transmission and reception. Because 100 MHz is part of the FM band, the technology for both driving a transmitter at this frequency and detecting very small signals has been well developed. Very sophisticated, compact, low-cost integrated circuits are available specifically to amplify weak signals in the FM band. Integrated circuits commonly available in the communications industry preferably perform the bulk of the analog signal processing performed by the computer component in preferred embodiments of this invention.

Although less preferable, other arithmetic methods of distance determination based upon phase differential may alternatively be used and are disclosed in, for example, U.S. Pat. No. 3,740,141 to DeWitt, Jr., U.S. Pat. No. 5,054,912 to Kuchel, and U.S. Pat. No. 5,589,928 to Babbitt et al., the disclosures of which are incorporated herein by reference.

The distance measuring component further preferably comprises, in addition to the computer component, one or more laser/sensor modules, each module comprising three basic elements: one or more transmitters, one or more receivers, and one or more reference frequency generators. The reference frequency generator preferably creates three frequencies, e.g., a 93±0.455 MHz transmit frequency; a 93 MHz receiver local oscillator frequency; and a 0.455 MHz reference frequency. Each of these frequencies has well-defined phases relative to each other, since they all should be synchronized to the same crystal resonator. During normal operation of apparatus of this invention, when the modulated laser light hits the target, a reflected or scattered beam returns and is detected by one or more photodiodes. This signal is amplified and mixed with the receiver frequency. Using the exemplary frequencies listed above, this results in a 0.455 MHz signal that maintains the phase information of the signal from the photodiode. This signal is then amplified, and its phase is determined relative to the 0.455 MHz reference signal in a second mixer followed by an averaging circuit. This measured phase output is related to the distance between the instrument and the object. The frequency of modulation of the transmitted laser beam can be changed between two values (0.455 MHz above and below the roughly 93 MHz receiver reference frequency) by an onboard processor, as can the phase of the 0.455 MHz reference signal (between 0 and 900). The processor may also monitor the phase output via a 12-bit A/D converter.

Figure 1:
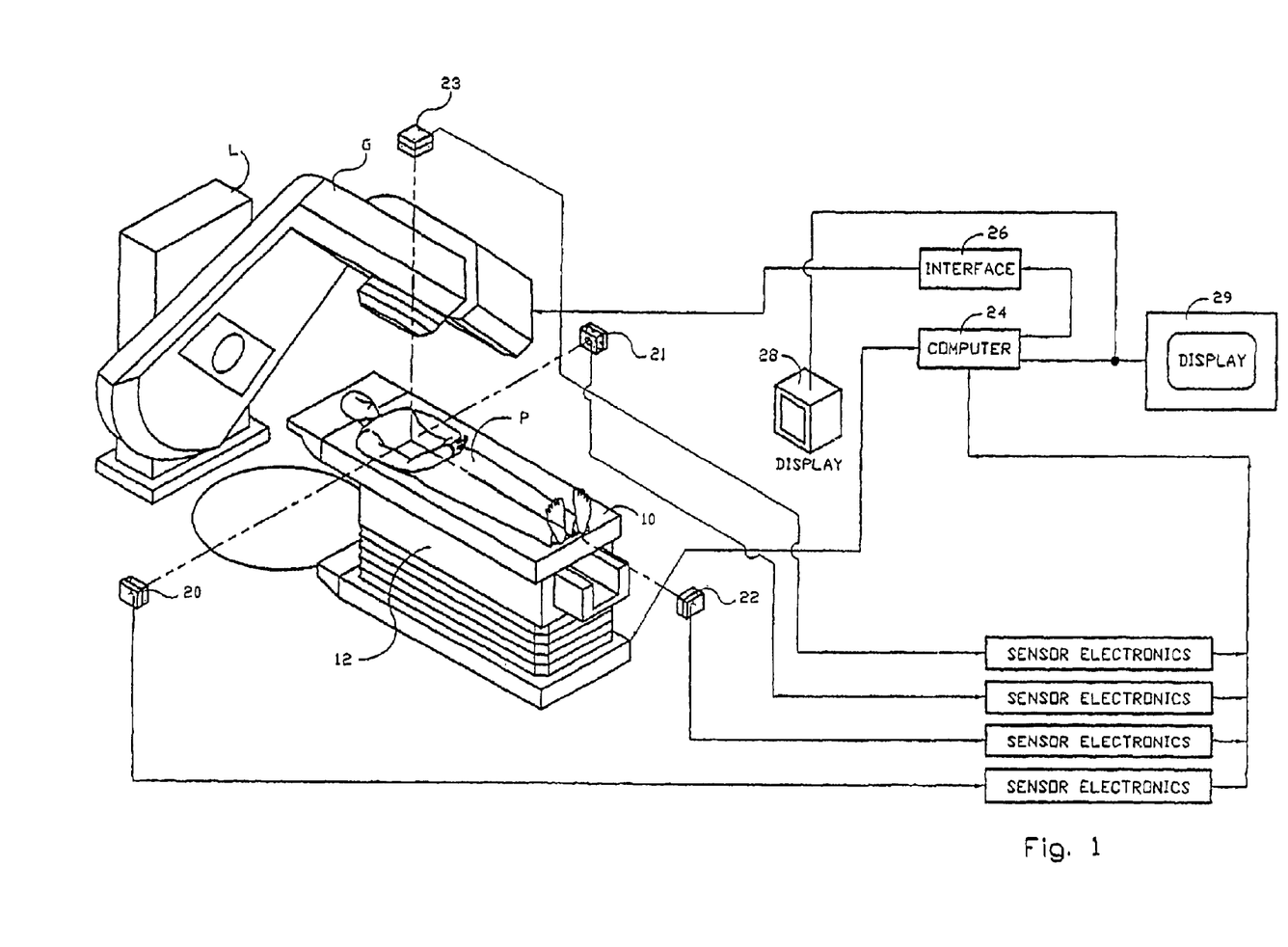
FIG. 1 is a schematic diagram and pictorial representation of preferred apparatus of this invention.
Figure 2:
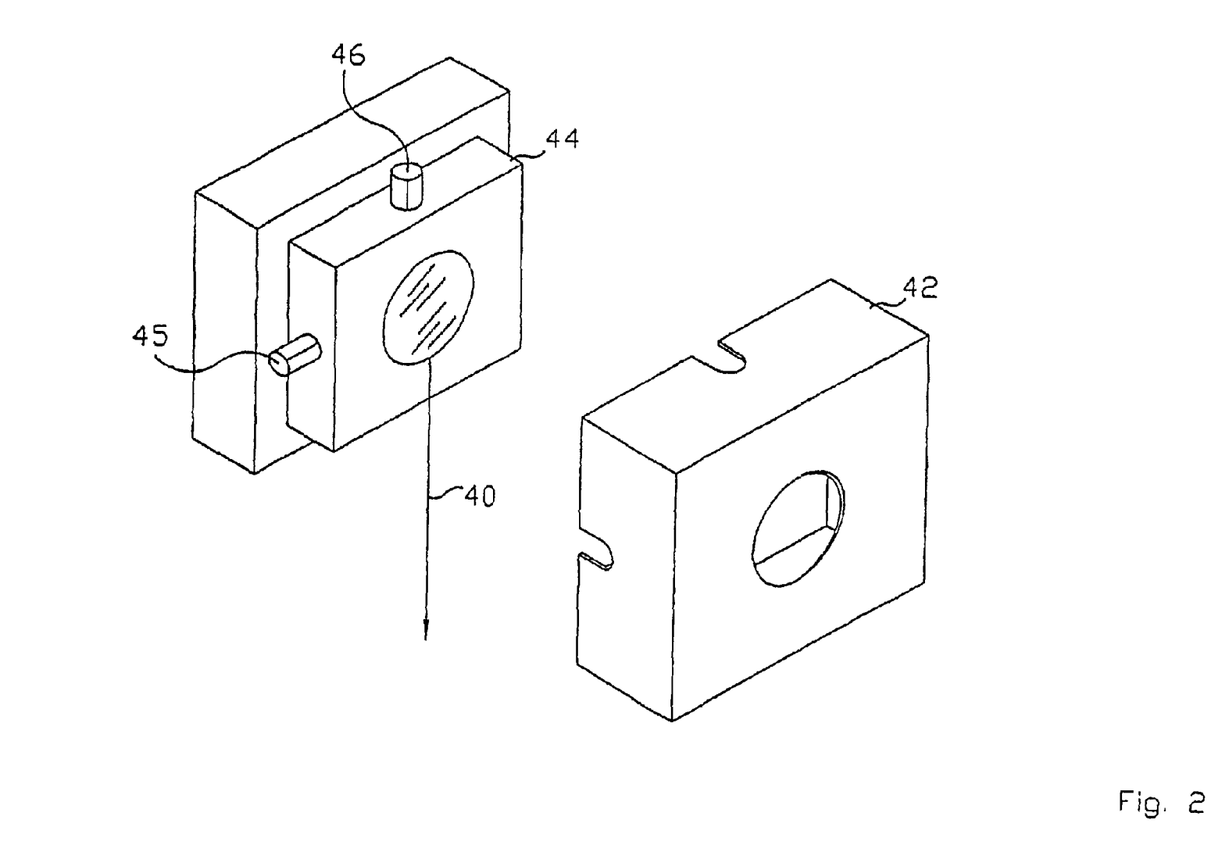
FIG. 2 is an elevated view in perspective of a laser/sensor module of the apparatus of FIG. 1.

Referring now to the drawings, it will be seen that FIGS. 1 and 2 illustrate a particularly preferred apparatus of this invention. In FIG. 1, a patient P is depicted lying upon a patient support in the form of platform 10 which is equipped to be position-adjusted via a controller 12. A linear accelerator L includes a rotatable gantry G. Four fiber optic laser/sensor modules 20, 21, 22 and 23 are disposed respectively upon three walls and the ceiling surrounding patient P. While four modules are present in the particularly preferred embodiment depicted to enhance the patient positioning in three dimensions, it should be understood that fewer or more than four modules can be used in apparatus and methods of this invention, so long as at least one is employed. Each of the laser/sensor modules is connected by respective fiber optic lines to sensor electronics 19. Generally, the sensor electronics 19 may be but are not necessarily comprised of a diode laser component, photodiode detector, fiber optic connections to the sensor module and phase-measuring electronics including a microprocessor to perform algorithmic functions. The sensor electronics 19 and the associated laser/sensor modules 20, 21, 22 and 23, as well as platform controller 12, are each directly controlled by a computer 24, while linear accelerator L is controlled by computer 24 through an interface 26. Computer 24 provides information visually through a display 28 within the treatment room, and a display 29 positioned outside of the treatment room, e.g., in a linear accelerator control console area. Typically in the use of the preferred embodiment depicted, patient P will be previously marked for treatment during a simulation, and the measured source to skin distances, i.e., the prior spatial positions for target area associated with each module, will be entered into computer 24. Alternatively, the prior spatial positions may be determined at the outset of use of the apparatus of this invention, the initial distance measurement for each target area constituting the prior spatial position for each target area against which all subsequent distance measurements are compared. When the prior spatial positions are determined using a previous simulation, patient P may be brought into the treatment room and placed upon platform 10, and the platform will be moved in the available translational directions until the source to skin distances measured by each of the laser/sensor modules input to computer 24 and displayed are synchronized with the source to skin distances previously determined during simulation.

As seen in FIG. 2, each of the laser/sensor modules in the particularly preferred embodiment depicted are fiber optic-based and include a connection 40 to sensor electronics 19, and a protective cover 42 for a sensor head 44 and a photodiode detector (not shown). In the embodiment depicted, each photodiode detector is connected to computer 24 through connections to sensor electronics 19. Each sensor head is comprised of a fiber optic connection to the laser module, a focusing lens for the outgoing laser light, a gathering lens for the reflected light, and a fiber optic connection to sensor electronics 19. Each module further includes a horizontal adjustment knob 45 and a vertical adjustment knob 46 for adjusting the laser beam vertically and horizontally over a range of 15 degrees in each dimension.

Figure 3:
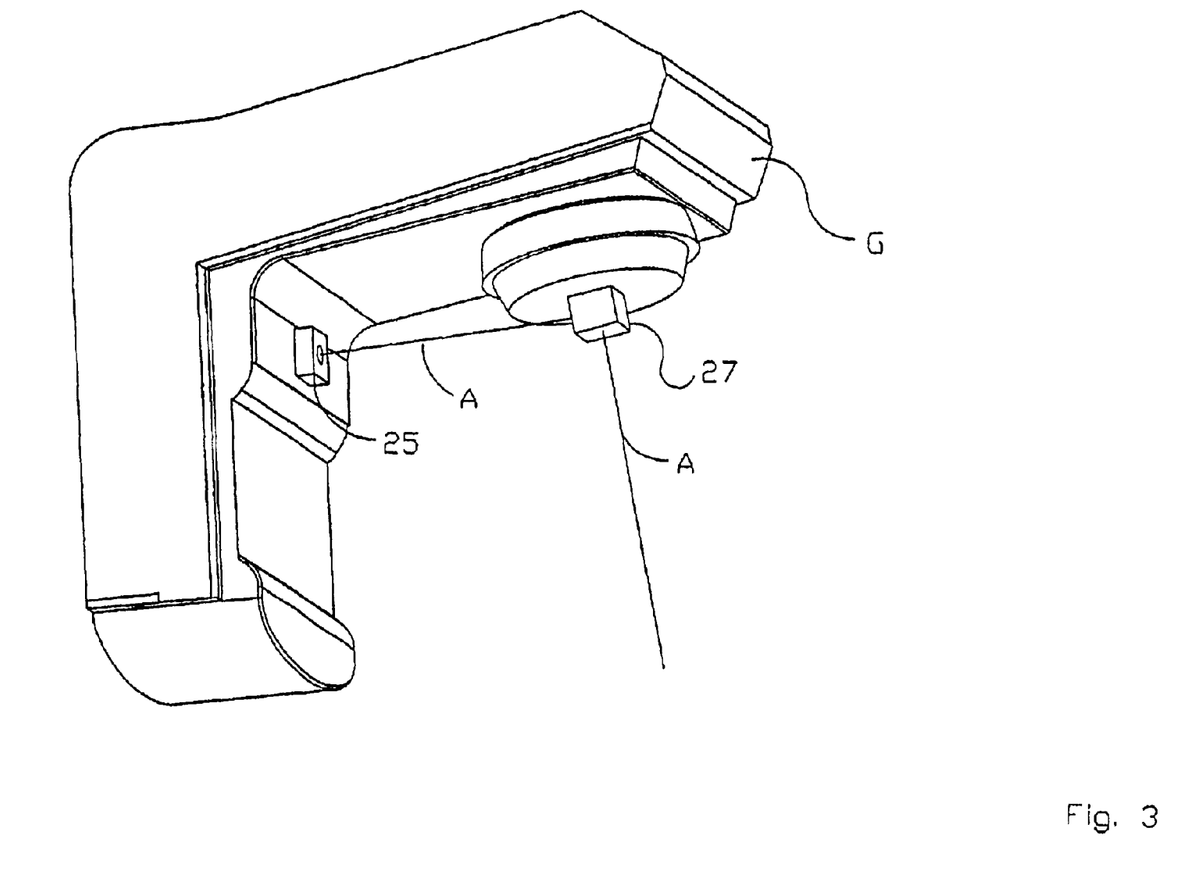
FIG. 3 is a lowered view in perspective of gantry-mounted components of another preferred embodiment of this invention.

In another particularly preferred embodiment illustrated in part in FIG. 3, an additional laser/sensor module 25 is mounted to gantry G and positioned to emit and receive laser beams along imaginary beam path A through a mirror-containing box frame 27 mounted to gantry G as illustrated in FIG. 3. In this way, the apparatus enables source to skin measurement regardless of gantry angle and gantry interference with the wall-mounted lasers/sensors. The laser/sensor module 25 may also be mounted inside the collimator head and use the light field mirror system to project the laser beam down the central axis of the accelerator.

It will now be appreciated that an apparatus of this invention may be employed to insure proper positioning of subjects receiving medical treatment or undergoing medical procedures. Non-limiting examples of such procedures and treatment include linear accelerator treatment, radiation therapy simulation and stereotactic radio surgery. With respect to linear accelerator treatment, for example, it will be noted that routine use of a linear accelerator involves measurements of source to skin distance and target area marking of the subject during a preliminary simulation which employs equipment and line-generating lasers to enable accurate marking. In using particularly preferred apparatus of this invention, as depicted in the accompanying figures, the marked subject is placed upon a support in a room equipped with four or more laser/sensor heads mounted in the room, preferably in the same position as the laser line-generating lasers used during simulation (e.g., left wall, right wall, sagittal wall, and ceiling or collimator head). The distance from each laser/sensor head to an associated area on the patient may be measured once the laser beams are incident upon that area and received by the photodiode detectors in each laser/sensor head. From this data, the source to skin distance may be determined, since the radiation source will have a fixed distance from the center of machine (gantry) rotation and the distance from the laser beam source to the center of machine rotation will be previously determined. Source to skin distance measurements taken during simulation, i.e., the prior spatial positions, can then be compared to the source to skin distance measurements measured by the laser/sensor modules, i.e., the later spatial positions, and the position of the support adjusted until all measured source to skin distances agree with those taken during the simulation. Upon proper placement of the patient, the machine operator may leave the radiation treatment room and receive real-time data regarding the source to skin distance while the machine is in operation, such data being displayed upon a monitor in the operator's console area.

In particularly preferred embodiments, the treatment machine maybe configured with a controller in communication with the measuring system so that the treatment machine delivers radiation to the subject only when the measured source to skin distances are within certain pre-selected distance tolerances. In one such preferred embodiment, such a controller receives commands from a programmed computer component of the measuring system. In this way, when the measured distances exceed the tolerances, the computer component signals the controller to trigger the machine to terminate radiation treatment. In another particularly preferred embodiment, an additional laser module may be installed at the treatment room ceiling to either periodically or constantly monitor the patient chest rise and fall due to respiration. Such information could be fed by the computer component of the measuring system to the controller of the machine to enable control of when, during the respiration cycle, radiation treatment is applied. Such respiratory-gated radiation therapy, where treatment would only occur at a predetermined portion of the breathing cycle, decreases the negative effects of organ motion during radiation treatment.

This invention is susceptible to considerable variation in its practice. Therefore, the foregoing description is not intended to limit, and should not be construed as limiting, the invention to the particular exemplifications presented above. Rather, what is intended to be covered is as set forth in the ensuing claims and the equivalents thereof permitted as a matter of law. As used in this disclosure, means-plus-function clauses are intended to cover the structures described herein as performing the cited function and not only structural equivalents but also equivalent structures.

What is claimed is:

1. Apparatus for detecting, measuring and correcting positional deviations of at least one area of a subject along one or more subject position axes, from a prior spatial position at a prior time to a later spatial position at a later time, which apparatus comprises:
   a) a distance-measuring component which at least
      1) continuously or intermittently gathers information corresponding to the spatial position of the area along a first subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area, and
      2) derives the later spatial position, and optionally the prior spatial position, of the area along the first subject position axis from the information gathered in 1);
   b) storage means for storing information corresponding to the prior and later spatial positions of the area;
   c) a support upon which the subject may lie;
   d) calculating means for determining, from the stored information, a deviation in spatial position of the area from its prior spatial position along the first subject position axis and translatory motion of the area which will restore the area to its prior spatial position along the first subject position axis, and generating at least one repositioning signal which transmits information corresponding to the translatory motion of either the support or the area necessary to restore the area to its prior spatial position along the first subject position axis; and
   e) a position controller which can at least reposition the support in response to the repositioning signal.

2. Apparatus as in claim 1 wherein the distance-measuring component further at least either simultaneously or sequentially repeats steps 1) and 2) of a) using a second amplitude modulated beam of radiation reflected by at least one area which is either the same as or different from the area in a), the second amplitude modulated beam of radiation having a modulation frequency which is not a harmonic of the first beam of radiation.

3. Apparatus as in claim 2 wherein a coherent radiation source is used to generate one or more of the beams of radiation, the frequency of the coherent radiation being less than the modulation frequency of the beam(s) of radiation so generated.

4. Apparatus as in any one of claims 2–3 wherein all of the beams of radiation originate from a single coherent radiation source.

5. Apparatus as in any one of claims 2–3 wherein each beam of radiation originates from its own corresponding coherent radiation source.

6. Apparatus as in claim 1 wherein a coherent radiation source is used to generate the first beam of radiation, the frequency of the coherent radiation being less than the modulation frequency of the beam(s) of radiation so generated.

7. Apparatus as in any one of claims 1–3 further comprising one or more display components which produce a visual image conveying area spatial position information.

8. Apparatus for detecting, measuring and correcting positional deviations of at least three areas on a subject along at least three corresponding subject position axes, from prior spatial positions at a prior time to later spatial positions at a later time, respectively, which apparatus comprises:
   a) a distance-measuring component which at least
      1) continuously or intermittently gathers information corresponding to the spatial positions of the areas along their respective first, second and third subject position axes, the information for each area being comprised of a phase difference between two oscillatory signals, the first of the signals A) corresponding to the intensity modulation of, or B) bearing a phase relationship to, a first amplitude modulated beam of radiation before the first beam of radiation is incident upon the respective area, and the second of the signals A) corresponding to the intensity modulation of, or B) bearing a phase relationship to, the first beam of radiation after the first beam of radiation has been reflected by the respective area, and
      2) derives the later spatial positions, and optionally the prior spatial positions, of the areas along the respective subject position axes from the information gathered in 1);
   b) storage means for storing information corresponding to the prior and later spatial positions of the areas;
   c) a support upon which the subject may lie; and
   d) calculating means for determining from the stored information a deviation in spatial position of the areas from their prior spatial positions and translatory motion of the areas which will restore the areas to their prior spatial positions, and generating at least one repositioning signal which transmits information corresponding to the translatory motion(s) of either the support or the areas which is (are) necessary to restore the areas to their prior spatial positions; and
   e) a position controller which can at least reposition the support in response to the repositioning signal.

9. Apparatus as in claim 8 wherein the distance-measuring component further at least simultaneously or sequentially repeats steps a)1) and a)2) using a second amplitude modulated beam of radiation reflected by at least one area which is either the same or different from one of the areas in a), the second amplitude modulated beam of radiation having a modulation frequency which is not a harmonic of the first beam of radiation.

10. Apparatus as in claim 9 wherein a coherent radiation source is used to generate one or more of the beams of radiation, the frequency of the coherent radiation being less than the modulation frequency of the beam(s) of radiation so generated.

11. Apparatus as in any one of claims 9–10 wherein all of the beams of radiation originate from a single coherent radiation source.

12. Apparatus as in any one of claims 9–10 wherein each beam of radiation originates from its own corresponding coherent radiation source.

13. Apparatus as in claim 8 wherein a coherent radiation source is used to generate the first beam of radiation, the frequency of the coherent radiation being less than the modulation frequency of the beam(s) of radiation so generated.

14. Apparatus as in any one of claims 8–10 further comprising one or more display components which produce a visual image conveying area spatial position information.

15. Apparatus for enhancing a position-adjustable subject support to enable detection of subject movement and real-time position adjustment to compensate for such subject movement, the support including a position controller, the apparatus comprising:
   a) a distance-measuring component which at least
      1) continuously or intermittently gathers information corresponding to the spatial position of the area along a first subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area, and
      2) continuously or intermittently derives the later spatial positions, and optionally the prior spatial positions, of the area along the first subject position axis from the information gathered in 1);
   b) storage means for continuously or intermittently storing information corresponding to the prior and later spatial positions of the area;
   c) calculating means for continuously or intermittently determining from the stored information a deviation in spatial position of the area from its prior spatial position and translatory motion of the area which will restore the area to its prior spatial position, and continuously or intermittently generating at least one repositioning signal which transmits information to the position controller, the transmitted information corresponding to instructions which may initiate the translatory motion of the support necessary to restore the area to its prior spatial position.

16. Apparatus as in claim 15 wherein the distance-measuring component further at least simultaneously or sequentially repeats steps (1) and (2) of a) using a second amplitude modulated beam of radiation reflected by at least one area which is either the same as or different from the area in (a), the second amplitude modulated beam of radiation having a modulation frequency which is not a harmonic of the first beam of radiation.

17. Apparatus as in claim 16 wherein a coherent radiation source is used to generate one or more of the beams of radiation, the frequency of the coherent radiation being less than the modulation frequency of the beam(s) of radiation so generated.

18. Apparatus as in any one of claims 16–17 wherein all of the beams of radiation originate from a single coherent radiation source.

19. Apparatus as in any one of claims 16–17 wherein each beam of radiation originates from its own corresponding coherent radiation source.

20. Apparatus as in claim 15 wherein a coherent radiation source is used to generate the first beam of radiation, the frequency of the coherent radiation being less than the modulation frequency of the beam(s) of radiation so generated.

21. Apparatus as in any one of claims 15–17 further comprising one or more display components which produce a visual image conveying area spatial position information.

22. In a linear accelerator machine which includes a position-adjustable support and support controller, the improvement which comprises apparatus for detecting, measuring and correcting positional deviations of at least one area of a subject of the accelerator machine along one or more subject position axes, from a prior spatial position at a prior time to a later spatial position at a later time, the apparatus comprising a) a distance-measuring component which at least
      1) continuously or intermittently gathers information corresponding to the spatial positions of the areas along their respective first, second and third subject position axes, the information for each area being comprised of a phase difference between two oscillatory signals, the first of the signals A) corresponding to the intensity modulation of, or B) bearing a phase relationship to, a first amplitude modulated beam of radiation before the first beam of radiation is incident upon the respective area, and the second of the signals A) corresponding to the intensity modulation of, or B) bearing a phase relationship to, the first beam of radiation after the first beam of radiation has been reflected by the respective area, and
      2) derives the later spatial positions, and optionally the prior spatial positions, of the areas along the respective subject position axes from the information gathered in 1);
   b) storage means for storing information corresponding to the prior and later spatial positions of the areas; and
   c) calculating means for determining from the stored information a deviation in spatial position of the areas from their prior spatial positions and translatory motion of the areas which will restore the areas to their prior spatial positions, and generating at least one repositioning signal which transmits information corresponding to the translatory motion(s) of either the support or the areas which is (are) necessary to restore the areas to their prior spatial positions.

23. The improvement according to claim 22 wherein the distance-measuring component further at least simultaneously or sequentially repeats steps (1) and (2) of a) using a second amplitude modulated beam of radiation reflected by at least one area which is either the same as or different from the area in a), the second amplitude modulated beam of radiation having a modulation frequency which is not a harmonic of the first beam of radiation.

24. The improvement according to claim 23 wherein a coherent radiation source is used to generate one or more of the beams of radiation, the frequency of the coherent radiation being less than the modulation frequency of the beam(s) of radiation so generated.

25. The improvement according to any one of claims 23–24 wherein all of the beams of radiation originate from a single coherent radiation source.

26. The improvement according to any one of claims 23–24 wherein each beam of radiation originates from its own corresponding coherent radiation source.

27. The improvement according to claim 22 wherein a coherent radiation source is used to generate the first beam of radiation, the frequency of the coherent radiation being less than the modulation frequency of the beam(s) of radiation so generated.

28. The improvement according to any one of claims 22–24 further comprising one or more display components which produce a visual image conveying area spatial position information.

29. A method of applying therapeutic radiation to a subject, the method comprising
   a) providing a support upon which the subject may lie;
   b) while the subject is on the support, continuously or intermittently gathering information corresponding to the spatial position of at least one area along at least one subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area;
   c) deriving the later spatial positions, and optionally the prior spatial positions, of the area along the subject position axis from the information gathered in b);
   d) storing information corresponding to the prior and later spatial positions derived in c);
   e) calculating from the stored information a deviation in spatial position of the area from its prior spatial position;
   f) determining, from the stored information and/or the deviation calculated in e), translatory motion of the area which will restore the area to the prior spatial position;
   g) generating at least one repositioning signal which transmits information corresponding to the translatory motion of either the support or the area which is necessary to restore the area to the prior spatial position; and
   h) repositioning the support in response to the repositioning signal.

30. A method according to claim 29 further comprising simultaneously or sequentially repeating steps b) and c) using a second amplitude modulated beam of radiation reflected by at least one area which is either the same as or different from the area in b), the second amplitude modulated beam of radiation having a modulation frequency which is not a harmonic of the first beam of radiation.

31. A method of applying therapeutic radiation to a subject, the method comprising
   a) providing a support upon which the subject may lie;
   b) while the subject is on the support, continuously or intermittently gathering information corresponding to the spatial position of at least two or more areas along respective subject position axes, the information so gathered with respect to each area being comprised of a phase difference between two oscillatory signals, the first of the signals A) corresponding to the intensity modulation of, or B) bearing a phase relationship to, a first amplitude modulated beam of radiation before the first beam of radiation is incident upon the respective area, and the second of the signals A) corresponding to the intensity modulation of, or B) bearing a phase relationship to, the first beam of radiation after the first beam of radiation has been reflected by the respective area;

c) deriving the later spatial positions, and optionally the prior spatial positions, of each of the areas along their respective subject position axes from the information gathered in b);

d) storing information corresponding to the prior and later spatial positions derived in c);

e) calculating from the stored information a deviation in spatial position of each of the areas from their prior spatial positions;

f) determining, from the stored information and/or the deviation calculated in e), translatory motion of each area which will restore the areas to their prior spatial positions;

g) generating at least one repositioning signal which transmits information corresponding to the translatory motion of either the support or the areas which is necessary to restore the areas to their prior spatial positions; and h) repositioning the support in response to the repositioning signal.

32. A method according to claim 31 further comprising simultaneously or sequentially repeating steps b) and c) using a second amplitude modulated beam of radiation reflected by at least one area which is either the same as or different from one of the areas in b), the second amplitude modulated beam of radiation having a modulation frequency which is not a harmonic of the first beam of radiation.

33. Apparatus for detecting, measuring and correcting positional deviations of at least one area of a subject along one or more subject position axes, from a prior spatial position at a prior time to a later spatial position at a later time, which apparatus comprises:

a) a distance-measuring component which at least 1) continuously or intermittently gathers information corresponding to the spatial position of the area along a first subject position axis, the information being comprised of a phase difference between two oscillatory signals, the first of the signals A) corresponding to the intensity modulation of, or B) bearing a phase relationship to, a first amplitude modulated beam of radiation before the first beam of radiation is incident upon the area, and the second of the signals A) corresponding to the intensity modulation of, or B) bearing a phase relationship to, the first beam of radiation after the first beam of radiation has been reflected by the area, and 2) derives the later spatial position, and optionally the prior spatial position, of the area along the first subject position axis from the information gathered in 1);

b) a storage component for storing information corresponding to the prior and later spatial positions of the area;

c) a support upon which the subject may lie;

d) a calculating component for determining, from the stored information, a deviation in spatial position of the area from its prior spatial position along the first subject position axis and translatory motion of the area which will restore the area to its prior spatial position along the first subject position axis, and generating at least one repositioning signal which transmits information corresponding to the translatory motion of either the support or the area necessary to restore the area to its prior spatial position along the first subject position axis; and e) a position controller which can at least reposition the support in response to the repositioning signal.

34. Apparatus as in claim 33 wherein the distance-measuring component further at least either simultaneously or sequentially repeats steps 1) and 2) of a) using a second amplitude modulated beam of radiation reflected by at least one area which is either the same as or different from the area in a), the second amplitude modulated beam of radiation having a modulation frequency which is not a harmonic of the first beam of radiation.

35. Apparatus as in claim 34 wherein a coherent radiation source is used to generate one or more of the beams of radiation, the frequency of the coherent radiation being less than the modulation frequency of the beam(s) of radiation so generated.

36. Apparatus as in any one of claims 34–35 wherein all of the beams of radiation originate from a single coherent radiation source.

37. Apparatus as in any one of claims 34–35 wherein each beam of radiation originates from its own corresponding coherent radiation source.

38. Apparatus as in claim 33 wherein a coherent radiation source is used to generate the first beam of radiation, the frequency of the coherent radiation being less than the modulation frequency of the beam(s) of radiation so generated.

39. Apparatus as in any one of claims 33–35 further comprising one or more display components which produce a visual image conveying area spatial position information.

* * * * *